United States Patent
Schneider

(10) Patent No.: US 8,490,625 B2
(45) Date of Patent: Jul. 23, 2013

(54) INTRAUTERINE DEVICE STRING

(76) Inventor: Laura Ann Schneider, Georgetown, TX (US)

( * ) Notice: Subject to any disclaimer, the term of this patent is extended or adjusted under 35 U.S.C. 154(b) by 337 days.

(21) Appl. No.: 12/759,616

(22) Filed: Apr. 13, 2010

(65) Prior Publication Data
US 2011/0247630 A1 Oct. 13, 2011

(51) Int. Cl.
*A61F 6/18* (2006.01)

(52) U.S. Cl.
USPC ............................ 128/840; 128/830; 128/839

(58) Field of Classification Search
USPC .......... 128/830, 833, 838–840; 424/430–433; 604/904
See application file for complete search history.

(56) References Cited

U.S. PATENT DOCUMENTS

| | | | | |
|---|---|---|---|---|
| 1,635,919 A | * | 7/1927 | Bartholomew | 128/839 |
| 1,896,071 A | * | 2/1933 | Clark | 128/839 |
| 3,993,057 A | * | 11/1976 | Ramwell | 128/833 |
| 3,993,058 A | * | 11/1976 | Hoff | 128/839 |

* cited by examiner

*Primary Examiner* — Patricia Bianco
*Assistant Examiner* — Keri J Nelson
(74) *Attorney, Agent, or Firm* — Laura Schneider

(57) ABSTRACT

An intrauterine device string is provided. The intrauterine device string has an elongated member with an upper portion, an intermediate portion, and a lower portion. The upper portion is configured to attach the elongated member to an intrauterine device. The intermediate portion is configured to extend through the endocervical canal of a female. The lower portion has a first curved portion configured to follow a contour of the external orifice of the cervix of a female. A second curved portion at an end of the lower portion has a memory-retaining material to prevent the second curved portion from passing through the external orifice of the cervix and to constrain the second curved portion to follow the contour of the outer portion of the cervix. The intermediate portion is configured to pass through a plane defined by three points on said second curved portion when in use.

16 Claims, 5 Drawing Sheets

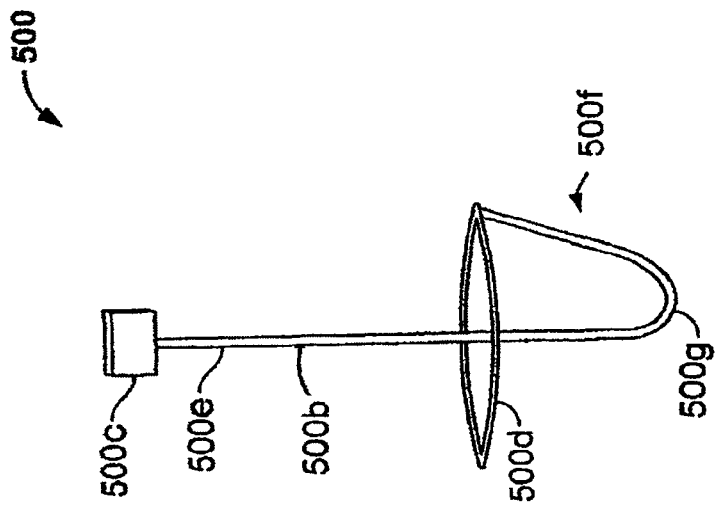
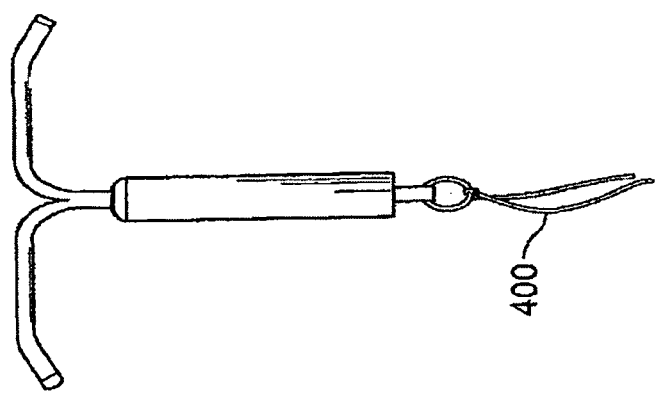
FIG. 2
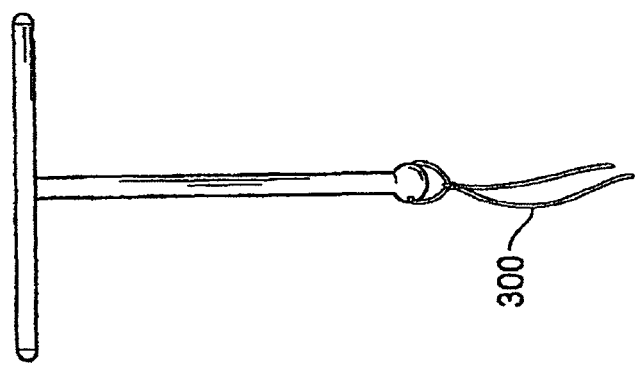
FIG. 1
(PRIOR ART)

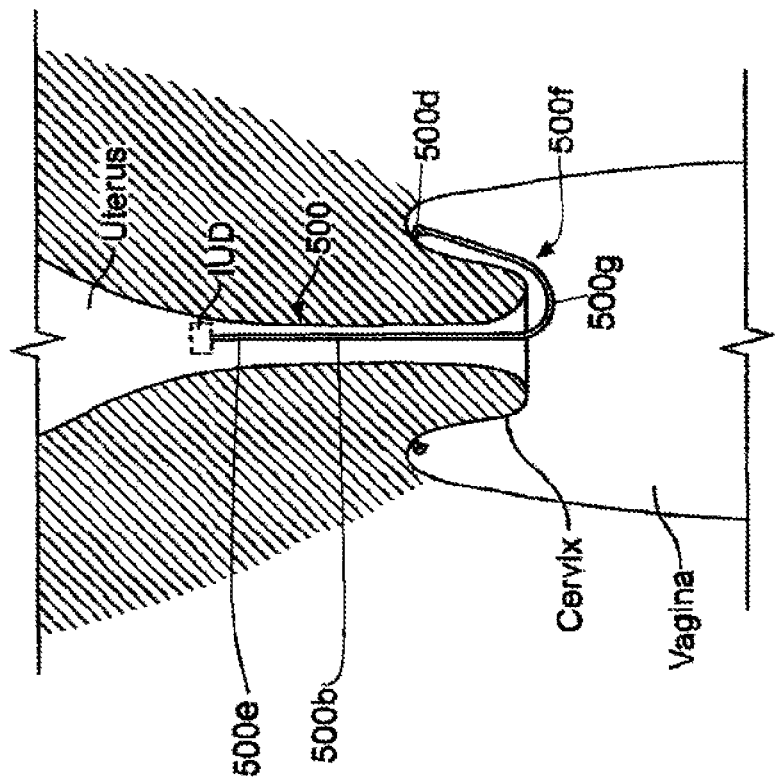
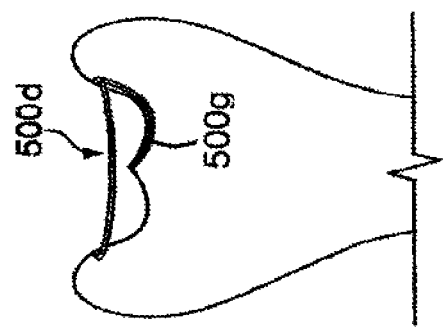

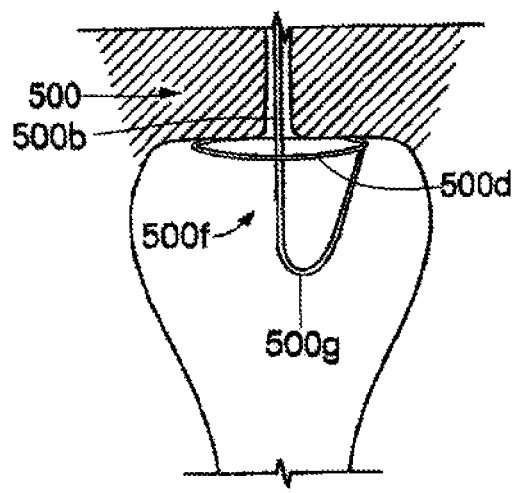
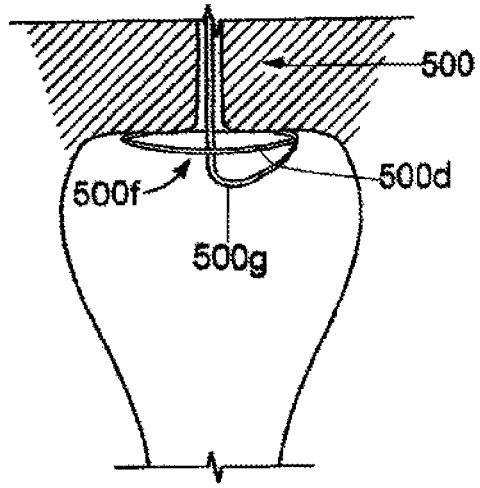
Fig. 5     Fig. 6
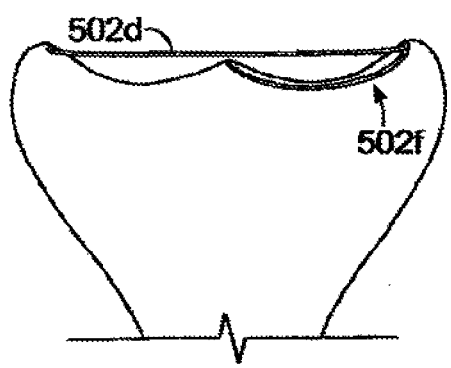
Fig. 7

INTRAUTERINE DEVICE STRING

CROSS REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING

Not Applicable

BACKGROUND

An intrauterine device, also known as an IUD, is a birth control device placed in the uterus as a method of reversible birth control. IUDs have been known and patented since the $19^{th}$ century. IUDs currently are T-shaped, and sized to fit entirely within the average adult female. Previous designs included IUDs having a shape of the number 7 or the capital greek letter omega, among others.

IUDs prevent pregnancy either through the slow release of a pregnancy-preventing substance such as copper or the hormone levonorgestrel into the uterus.

As exemplified in FIG. 1, IUDs currently on the market are manufactured with one or more strings extending from the bottom of the IUD. These strings are provided to serve the purposes of IUD adjustment and removal. When the body of the IUD is placed in the uterus, the string(s) extend through the cervix and, ideally at least, remain positioned in the vaginal cavity.

The strings are manufactured of any materials known to be safe when placed in the body over an extended period of time such as a monofilament polyethylene string or a metal-coated string.

It is believed that the metal layer prevents bacteria and other infection-causing agents from entering the cervix and traveling to the uterus, or at least reduces the distance that these agents travel into the cervix.

After placing the IUD in the uterus, physicians cut the strings to a length that they believe is comfortable for the woman. The exact preferred length, however, is merely a guess. If a string is left too long, it can become displaced to the point that it may hang out of the woman's vagina, become entangled with tampons, or cause discomfort for the woman's sex partner.

It is also common for physicians to wrap the string(s) around the cervix in an effort to minimize distraction for women and their sex partners, but this practice is largely dependent on physician training or preference, and, in any case, there is no guarantee that the string will remain in the wrapped position.

Further, if the string is cut too short, or at an angle at the tip, it can cause serious discomfort or even pain for both the users and their partners.

In all cases, there is a known risk that the position of the IUD changes after insertion. The IUD may slide too far in the uterus, thus decreasing the effectiveness of the IUD. This also increases the difficulty of extraction because the string(s) cannot be located by the user or the physician.

In all cases, it is also known that the IUD may be expelled without the user noticing, thus putting her at risk of pregnancy without knowing she is at risk.

It is also known that when a user wears tampons, she can accidentally pull the IUD out or out of the ideal position when extracting the tampon because the strings of traditional IUD's become entangled or otherwise semi-attached to the tampon.

It is also known that a woman's uterus does not remain in a fixed location within her body. Particularly in women with weak cardinal ligaments and other supporting structures (e.g., uterosacral ligaments), the location of the entire uterus in relation to that of the vagina changes, not just over a long period of time, but sometimes over the course of a single day. Because the distance that the uterus drops can be significant, even as much as 5 cm, an IUD string cut to fit perfectly in the morning hours—when a woman's structure is strong—may actually hang out of the vagina by the afternoon, after the uterus has dropped in the course of the day.

No traditional IUD cures all of these deficiencies and provides a person a simple way of holding an IUD in place without interfering with sex and also provides a simple way of extracting the IUD.

SUMMARY

The present invention relates to an intrauterine device string for attachment to an intrauterine device fitted within a female, the female having a cervix comprising an endocervical canal and an external orifice, the intrauterine device string comprising an elongated member with an upper portion, an intermediate portion, and a lower portion; wherein said upper portion is configured to attach said elongated member to the intrauterine device, wherein said intermediate portion is configured to extend through the endocervical canal, and wherein said lower portion comprises a first curved portion configured to follow a contour of the external orifice of a cervix; and a second curved portion at an end of said lower portion configured to prevent said second curved portion from passing through the external orifice of the cervix.

The present invention also relates to a method for attaching an intrauterine device string to an intrauterine device comprising: providing an elongated member with an upper portion, an intermediate portion, a lower portion; inserting said elongated member into the cervix such that the intrauterine device rests in the uterus; attaching said elongated member to the intrauterine device; positioning said elongated member in the cervix such that said second curved portion rests outside of the external orifice of the cervix; and adjusting said second curved portion wherein said elongated member is stabilized in the cervix.

BRIEF DESCRIPTION OF THE DRAWINGS

FIG. 1 illustrates traditional intrauterine devices with intrauterine device strings attached.

FIG. 2 is a front view of the object according to one set of embodiments of the present invention.

FIG. 3 is a cross-sectional view of the object according to one embodiment of the present invention positioned in the user's body.

FIG. 4 is a sectional view of one embodiment of the invention positioned in the user's body.

FIG. 5 is a sectional front view of one embodiment of the present invention positioned in a woman who has had a portion of her cervix removed.

FIG. 6 is a sectional front view of an alternative embodiment of the present invention positioned in a woman who has had a portion of her cervix removed.

FIG. 7 is a sectional view of an alternative embodiment of the invention positioned in the user's body.

DESCRIPTION

Figure 8:
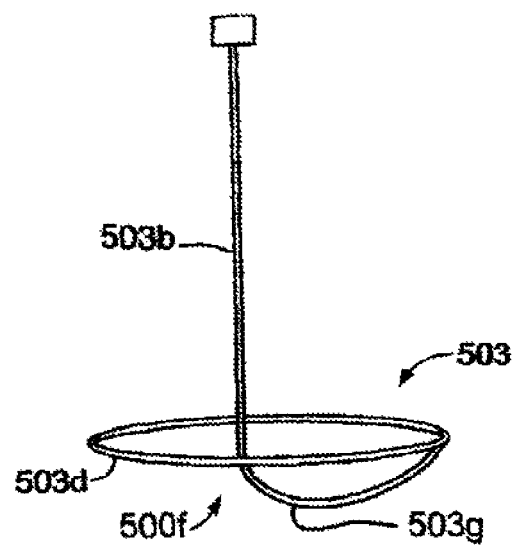
FIG. 8 is a front view of an alternative embodiment of the invention.

The present invention relates to an intrauterine device string for attachment to an intrauterine device fitted within a female, the female having a cervix comprising an endocervical canal and an external orifice, the intrauterine device string comprising an elongated member with an upper portion, an intermediate portion, and a lower portion; wherein said upper portion is configured to attach said elongated member to the intrauterine device, wherein said intermediate portion is configured to extend through the endocervical canal, and wherein said lower portion comprises a first curved portion configured to follow a contour of the external orifice of a the cervix; and a second curved portion at an end of said lower portion configured to prevent said second curved portion from passing through the external orifice of the cervix.

The present invention also relates to a method for attaching an intrauterine device string to an intrauterine device comprising: providing an elongated member with an upper portion, an intermediate portion, a lower portion; inserting said elongated member into the cervix such that the intrauterine device rests in the uterus; attaching said elongated member to the intrauterine device; positioning said elongated member in the cervix such that said second curved portion rests outside of the external orifice of the cervix; and adjusting said second curved portion wherein said elongated member is stabilized in the cervix.

The term "string" may refer to any flexible to semi-flexible elongated material resembling the shape, form, or configuration of a string, twine, wire, strand, cord, thread, or fiber. It is understood that the term "string", when used to reference a device for attachment to an IUD, or as part of an IUD, is meant to reference a device which is suitable for extracting an IUD.

FIG. 1 illustrates traditional IUD's. Traditional IUD strings 300 and 400 are depicted.

FIG. 2 illustrates one embodiment of the invention. The elongated member 500 has an upper portion 500e, an intermediate portion 500b and a lower portion 500f wherein the upper portion 500e comprises a connecting means 500c, the intermediate portion 500b is configured to extend through an endocervical canal, and the lower portion 500f comprises a first curved portion 500g, and at the end of the lower portion 500f there is a second curved portion 500d. In this embodiment, the intermediate portion 500b passes through a plane defined by three points on the second curved portion 500d. In this embodiment the second curved portion 500d is a closed loop. In another embodiment, the second curved portion 500d is a closed loop but is not spherical. In another embodiment the second curved portion 500d is a partially open loop or not a loop. The connecting means can be any suitable means to connect the elongated member 500 to an IUD such as by suction, snap, any type of fastener, any type of fastening element, female fastener, buckle, adhesive, mechanical locking system or those depicted in FIG. 1.

In another embodiment, the second curved portion 500d is flexible. In one embodiment, the second curved portion 500d is configured to follow the contour of the outer portion of the cervix. Women's cervixes can vary in diameter from 2 cm to 8 cm. Some women have scar tissue around the cervix. Some women have the cervix removed entirely. Thus in one embodiment, the second curved portion 500d can self-adjust to follow the contour of any size or shape cervix after it is inserted into the proper position in the cervix area. In another set of embodiments, the elongated member 500 further comprises an adjusting means for said second curved portion 500d. In this embodiment the adjusting means configures the second curved portion 500d to accommodate a larger cervix or a partial cervix. The adjusting means can also configure the second curved portion 500d to accommodate a woman who has had the cervix removed. In another embodiment, the second curved portion 500d is not spherical and can be oblong, oval, a hook, spiral, a conical helix, trapezoidal, triangular or any shape that is comfortable or any shape suitable to prevent the elongated member 500 from moving into a position that is not comfortable or where the second curved portion 500d passes through the external orifice of the cervix. In another embodiment, the second curved portion 500d is a plurality of curved portions.

The intermediate portion 500b is long and thin enough to extend through the length of a woman's endocervical canal comfortably on a long term basis. The intermediate portion 500b has any diameter suitable where the elongated member 500 can rest comfortably on a long term basis in the body, preferably around 1 mm in diameter, which is a common string size associated with IUDs currently on the market.

In one embodiment, the elongated member 500 is one continuous piece. In another embodiment, the elongated member 500 is comprised of multiple pieces. In another embodiment, the elongated member 500 is flexible. In another embodiment, the first curved portion is flexible. The flexibility is measured by the force to bend. The maximum force to bend is 1.5 lb-force, preferably under 1 lb-force. In another embodiment, the elongated member 500 comprises a metal coating. In another embodiment, the second curved portion 500d is 0.5 or any suitable force to be where woman is comfortable. The first curved portion 500g is flexible or semi-flexible. The first curved portion 500g is moveable to one of a plurality of different positions on said lower portion 500f.

The length of women's endocervical canals do not vary greatly from woman to woman. In one embodiment, the elongated member 500 is 4 cm to 5 cm in length, or any length suitable for women having an anatomy that is particularly different, normally as a result of surgery. One example is found in women who have had surgery to remove the cervix, usually due to cervical cancer. In this case, the endocervical canal is shorter by as much as around 2 cm. In these cases, the term "cervix" as used herein should be construed as including the external orifice of the uterus.

FIG. 3 illustrates the elongated member 500 independently in the natural form and positioned in the cervix wherein the upper portion 500e is configured to attach the elongated member 500 to an intrauterine device, the intermediate portion 500b is configured to extend along the cervix, and the lower portion 500f comprises a first curved portion 500g configured to follow a contour of an external orifice of a cervix. In cases where a portion of the cervix is removed or the entire cervix is removed, the first curved portion 500g is configured to follow a contour of the external orifice of a uterus.

FIG. 4 illustrates another embodiment wherein the first curved portion 500g is following the contour of the external orifice of the cervix and the second curved portion FIG. 4—500 is following the contour of the outer part of the cervix. In another embodiment, the shape of the second curved portion FIG. 4—500 can be changed to any suitable shape wherein the second curved portion FIG. 4—500 does not does not pass through the external orifice of the cervix. The shape of the second curved portion FIG. 4—500 is also suitably shaped wherein the elongated member FIG. 2—500 rests comfortably in the cervix and is configured to prevent the elongated member 500 from entering too far into the uterus.

FIG. 5 illustrates another embodiment wherein the elongated member 500 is positioned in the cervix and the intermediate portion 500*b* passes through a plane defined by three points on the second curved portion 500*d*, and the lower portion 500*f* comprises a first curved portion 500*g* which is lower than the second curved portion 500*d*. In this embodiment, the second curved portion 500*d* rests at the entrance of the external orifice of the cervix.

FIG. 6 illustrates another set of embodiments wherein the elongated member 500 is positioned in the cervix and the first curved portion 500*g* has a different shape and is in a different position on the lower portion 500*f* relative to the shape and location of the first curved portion 500*g* depicted in FIG. 5. In this embodiment, the first curved portion 500*g* is flexible wherein the first curved portion 500*g* can change shape as the uterus and cervix changes shape, and the second curved portion 500*d* remains rigid enough to prevent the elongated member 500 from entering the uterus. In another embodiment, the first curved portion 500*g* is able to be moved to one of a plurality of different positions on said lower portion 500*f*.

In another embodiment the first curved portion 500*g* comprises a memory retaining material. In another embodiment the elongated member 500 comprises a memory-retaining material. In another embodiment, the second curved portion 500*d* comprises a memory-retaining material. In yet another embodiment, the second curved portion 500*d* could be one of many shapes such as a spiral, or a hook, or a helix or a plurality of curved portions. In this embodiment, the first curved portion 500*g* further comprises a malleable metallic inner core. In another embodiment, the second curved portion 500*d* is thicker in diameter than the upper portion 500*b*.

In another embodiment, the second curved portion 500*d* further comprises a proximal end and a distal end wherein the proximal end is closer to the first curved portion 500*g*. In this embodiment, the second curved portion 500*db* increases in thickness from said proximal end to said distal end.

FIG. 7 illustrates another embodiment where the second curved portion 502*d* has a shape wide enough to encompass the outer portion of the external orifice of the cervix. The first curved portion 502*f* is depicted as following the contour of the external orifice of the cervix.

FIG. 8 illustrates another embodiment of the invention where the first curved portion 503*g* is in a different location on the lower portion 500*f* than as illustrated in FIG. 1. The first curved portion 503*g* is closer to the distal end of the lower portion 500*f* relative to the location on the lower portion 500*f* in FIG. 1.

Figure 9:
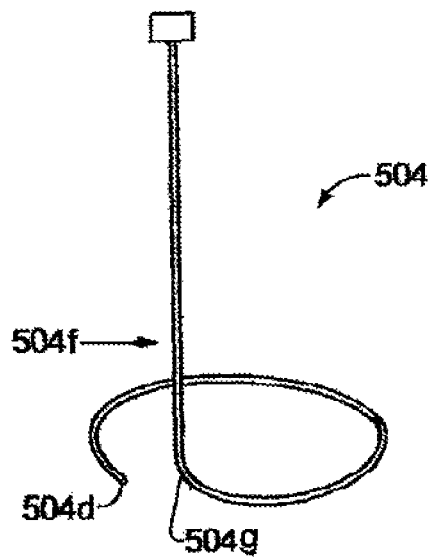
FIG. 9 is a perspective view of an alternative embodiment of the invention.

FIG. 9 illustrates another embodiment wherein the second curved portion 504*d* is not a closed loop. In this embodiment, the elongated member 504 further comprises a means for adjusting (not depicted) the shape of the second curved portion 504*d*. Furthermore, the first curved portion 504*g* is at the furthest point closest to the distal end of the lower portion 504*f*.

Figure 10:
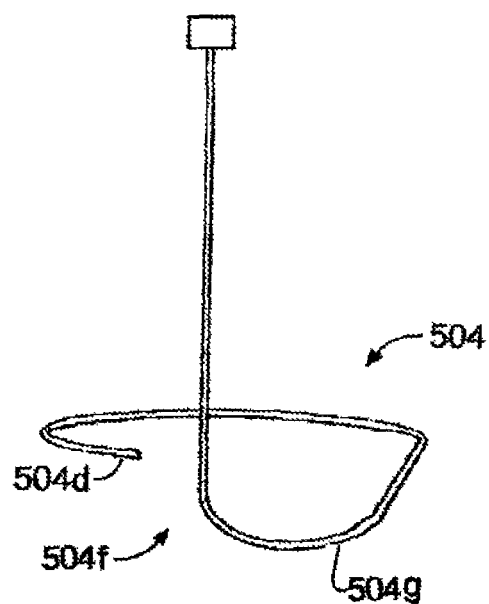
FIG. 10 is a front view of an alternative embodiment of the invention.

FIG. 10 another shape of the embodiment of FIG. 9. In FIG. 10, the second curved portion 504*d* is not a closed loop but the first curved portion 504*g* is closer to the proximal end of the lower portion 504*f*.

The first curved portion 500*g* in the invention serves up to three purposes, depending on the embodiment and material chosen. An intrauterine device string having a very flexible first curved portion 500*g* can be very useful for women who have had the cervix removed, as depicted in FIG. 5, as the first curved portion 500*g* can, in effect, collapse against the wall separating the vagina from the uterus. If a very flexible first curved portion 500*g* is chosen, a closed loop for the second curved portion 500*d* is preferred.

In one set of embodiments where the first curved portion 500*g* is semi-flexible, it serves three purposes. First, because it curves the lower portion 500*f* of the elongated member 500 towards the back of the portio vaginalis, the first curved portion 500*g* in conjunction with the second curved portion 500*d* prevents the intrauterine device from sliding further into the uterus as depicted in FIG. 3 and FIG. 5. In this embodiment, the second curved portion 504*d* is a partially closed loop as depicted in FIG. 9.

Secondly, a semi-flexible first curved portion 500*g* assists with positioning the second curved portion 500*d* further from the vaginal opening than the portio vaginalis, preferably by about 2 cm. It is thought by the inventor that this form increases the comfort for both the user and her sexual partner, as this would reduce the sensation of a foreign object being in the vagina, a common complaint with current intrauterine devices on the market.

In the case of a woman who has had a portion of the cervix removed, a semi-flexible first curved portion 500*g* would push the second curved portion 500*d* into the lining of the uterus slightly, although this is not depicted in FIG. 5*a*.

Finally, a semi-flexible first curved portion 500*g* in the invention ensures that the intrauterine device string of the present invention does not get entangled with tampons placed in the vagina, thus decreasing the risk of the IUD being pulled out when the user extracts a tampon.

The first curved portion 500*g* is shown in FIGS. 2-5 as being approximately 180 degrees and in association with the second curved portion 500*d*. In one embodiment, the second curved portion 500*d* is a closed loop having a diameter of around 2 cm, which is the approximate diameter of a woman having a small cervix, usually one who has not given birth. With a semi-flexible first curved portion 500*g*, some deformation is possible, and preferred, to allow the shape to conform to the user, as shown in FIG. 4.

The first curved portion 500*g* can, however, be much less than 180 degrees, as shown in FIG. 5, FIG. 6 and FIG. 7. This would accommodate an embodiment where the second curved portion 500*d* is a closed loop having a larger diameter.

The first curved portion 500*g* can be as small as 90 degrees, which would place the second curved portion 500*d* approximately even with the tip of the cervix.

In another embodiment, the first curved portion 500*g* is used in association with a larger second curved portion 500*d* that is a closed loop and the length of the lower portion 500*f* is necessarily longer than it would be in the case of a smaller loop.

In another set of embodiments, the present invention is manufactured with varying curved portion diameters, curved portion angles, and lengths of shorter lower portions to accommodate various body types, as women's cervical walls vary from about 1 cm in thickness to about 4 cm. It is also possible to measure each woman individually, and select an intrauterine device string to fit her body type.

In another set of embodiments, a material of suitable semi-rigidity is chosen that will allow the use of a one-size-fits-all approach. That is, the first curved portion 500*g* should be deformable enough that, after insertion, it will comfortably deform to accommodate a cervix having a larger wall thickness than the first curved portion 500*g* diameter chosen, as well as to deform as the woman's shape changes over time, as it is known that the wall of a woman's cervix generally becomes larger over time.

The user should not feel a rigid intrauterine device string passing around contour of the wall of her cervix. The exact rigidity chosen should be based upon studies in which women indicate the comfort level of the first curved portion 500g having various rigidities.

In another embodiment, the first curved portion 500g diameter is between 0.5 and 1.5 cm, as measured when the string is not being manipulated. This is slightly smaller than the average thickness of the wall of a woman's cervix.

This combination of the first curved portion 500g angle, diameter and rigidity would enable a one-size-fits-all approach, and hence reduce manufacturing costs, as well as the cost of patient care due to the lowered time spent with each individual.

It is also contemplated that the first curved portion 500g include means for adjusting the location and/or angle of the first curved portion 500g. This could be achieved, for example, by manufacturing the invention with a central metal core which would enable the physician to adjust the first curved portion 500g after placing the IUD in the woman's uterus. The metal core should be sized for comfort, and the particular material chosen should allow for ease of manipulation without compromising the other desired effects of a semi-flexible first curved portion 500g. The metal core does not necessarily have to exist throughout the length of the string. It could, for example, be present in only the portion in and near the first curved portion 500g, although, to ease manufacturing, the metal core may be through the entire length of the string.

In embodiments where the second curved portion 500d is a closed loop, the second curved portion 500d is at the distal end of the lower portion 500f and has a diameter large enough to accommodate the outer circumference of the cervix.

In other embodiments, the second curved portion 500d is a partial or open loop as depicted in FIG. 9 and FIG. 10. If the second curved portion 500d has suitable rigidity to prevent displacement of the IUD into the uterus and is comfortable for long-term use, then an open loop is preferred, as this would enable the use of a one-size-fits-all approach, that is, the invention could be manufactured using a semi-flexible material in the open loop that would fit tightly around a cervix as small as 2 cm, yet deform comfortably to fit partially around a cervix as large as 7 cm.

A blunt end of the open loop would assist in improving comfort, by preventing the second curved portion 500d from "digging into" the woman's cervical wall.

In embodiments where the second curved portion 500d is a closed loop, it can be manufactured with varying diameters to accommodate different individuals, between about 2.5 cm and 7 cm, allowing the physician to select an appropriate size for each patient. These sizes are suggestions for starting points; the actual sizes chosen may vary based upon studies, with comfort and population distribution as the focus.

Alternatively, the means for adjusting the shape and/or diameter of the second curved portion 500d when it is a closed loop may be provided to allow the closed loop to be adjusted to fit each individual perfectly. There are countless possible ways in which this can be achieved. Examples include ratcheting or snap-lock mechanisms in which the diameter of the closed loop is adjusted by the physician and locked. It can also be semi-flexible as long as it is not so rigid that it would prevent insertion or cause discomfort for women. In another embodiment, the second curved portion 500d has a thickness of around 2 mm or any suitable thickness that would provide the most comfort on a long-term basis.

In another embodiment, the lower portion 500f comprises a proximal end and a distal end and further comprises a first curved portion 500g with a diameter of 1.5 cm and a second curved portion of 500d, which is located at the distal end of the lower portion 500f, that is a closed loop with a larger diameter relative to the first curved portion 500g such as 7 cm. In this embodiment, the lower portion 500f is preferably rigid enough to help keep the second curved portion 500d located further from the vaginal opening than the tip of the cervix, yet flexible enough to increase comfort, and possibly allow insertion using plunger tubes currently on the market.

In another set of embodiments, the elongated member 500 should be manufactured of a semi-flexible to semi-rigid material, such as a plastic or memory-retaining metal or plastic; however, other materials may be selected, as long as they are suitable for the purpose of long-term placement in the vagina, endocervical canal, and uterus. The exact material selection should be made in accordance with test results in individuals. In yet another embodiment, the elongated member 500 comprises a metal coating.

Selection of a more rigid material improves long-term positioning, while it is thought that a more flexible material is more comfortable for the user and her sexual partner.

A more flexible material also assures the ease of insertion. Insertion of an intrauterine device with a string attached normally requires that the intrauterine device and string be pushed through a thin plunger tube. The more flexible material would allow the current methods and devices for IUD insertion to remain in use, as the string of the present invention would travel through the tube and spring in to the natural position after it is in place and the tube is extracted.

In any case, the elongated member 500 is preferably flexible enough to allow the string to deform enough during insertion and extraction to prevent discomfort for the user.

In another set of embodiments, the rigidity of the elongated member 500 varies throughout the elongated member. For example, the upper and intermediate and lower portions of the elongated member may be designed to conform to a woman's cervix, and should therefore be less rigid than the second curved portion 500d. The second curved portion 500d may be intended to prevent the intrauterine device from slipping into the uterus, as well as expulsion of the intrauterine device without the user's knowledge, and should therefore be more rigid relative to the other portions of the elongated member.

In another embodiment, the second curved portion 500d could be provided separately from the elongated member 500. For example, the elongated member 500 can be manufactured with a semi-flexible first curved portion 500g, and, after placing the intrauterine device in the uterus, the physician could attach the second curved portion 500d having a diameter suitably sized to fit the individual. The means for attachment must be provided.

When it comes to comfort of the user and her partner the thickness of the second curved portion 500d should be as small as possible to minimize any sensation of a foreign object in the vagina. The thickness and rigidity must, however, ensure that the second curved portion cannot deform so much that it could slip inside the woman's cervix.

While this invention is discussed primarily as relating to intrauterine devices, it is possible for this invention to be used with other intrauterine devices, such as an intrauterine fallopian tube occlusion device. It should also be understood that, although features are depicted and/or discussed in a limited number of embodiments, the features of the embodiments can be mixed and matched between different embodiments, with the goal of achieving maximum comfort for women and their partners, along with reasonable manufacturing and health care costs.

It is further contemplated that the present invention be used with other intrauterine devices in female animals, in particular animals having a single uterus.

When used in animals, the form of the curved portions of the present invention remains the same, but the sizing is modified to accommodate the thickness and outer diameter of the cervical wall, as well as the distance that the cervix extends into the vagina. The rigidity should also be modified to account for the stronger muscles associated with larger animals.

In another set of embodiments, the invention comprises an elongated member 500 comprising an upper 500e, intermediate 500b and lower 500f portion wherein the lower portion 500f further comprises a proximal end and a distal end and a first curved portion 500g, and there is a second curved portion 500d at the distal end of the lower portion 500f. In this set of embodiments, the second curved portion 500d is a closed loop. The upper portion 500e comprises a suitable means for attachment to the base of an intrauterine device by any means known in the industry. The length of the elongated member 500 is preferably about 4.5 cm. The diameter of the first curved portion 500g is preferably about 1.5 cm, and the diameter of the second curved portion 500d is preferably about 2.5 cm, 4 cm, or 7 cm. The angle of the first curved portion 500g is preferably sized to place the elongated member running through the second curved portion 500d. The elongated member 500 is preferably semi-flexible and metal coated. The elongated member 500 preferably has a metal inner core suitable for enabling a physician to move the location of the first curved portion 500g to one of a plurality of different positions on the lower portion 500f after inserting the intrauterine device in a user. The elongated member 500 preferably can be manipulated to fit inside a plunger tube for inserting into the user.

Another embodiment of the present invention is a kit comprising an intrauterine device string comprising: an elongated member with an upper portion, an intermediate portion, a lower portion; wherein said upper portion is configured to attach said elongated member to an intrauterine device, wherein said intermediate portion is configured to extend through an endocervical canal, and wherein said lower portion comprises a first curved portion configured to follow a contour of an external orifice of a cervix; and a second curved portion at the end of said first curved portion configured to prevent said second curved portion from passing through the external orifice of the cervix. The upper, intermediate and lower portions may be deformed and/or compacted for packaging, shipping or storage.

Another embodiment of the present invention is a method for using an intrauterine device string comprising an intrauterine device string comprising: an elongated member with an upper portion, an intermediate portion, a lower portion; wherein said upper portion is configured to attach said elongated member to an intrauterine device, wherein said intermediate portion is configured to extend through an endocervical canal, and wherein said lower portion comprises a first curved portion configured to follow a contour of an external orifice of a cervix; and a second curved portion at the end of said first curved portion configured to prevent said second curved portion from passing through the external orifice of the cervix, comprising the steps of opening the package of the intrauterine device string, inserting the elongated member into the cervix, positioning said elongated member so that the second curved portion rests comfortably at the external orifice of the cervix, or if necessary, around the outer circumference of the cervix, stabilizing said elongated member by adjusting the first and second curved portions; and adjusting said first curved portion so that the elongated member rests comfortably.

Another embodiment of the present invention is a method for holding an intrauterine device in place once inserted comprising the steps of connecting an elongated member with an upper portion, an intermediate portion, a lower portion; wherein said upper portion is configured to attach said elongated member to an intrauterine device, wherein said intermediate portion is configured to extend through an endocervical canal, and wherein said lower portion comprises a first curved portion configured to follow a contour of an external orifice of a cervix; and a second curved portion at the end of said first curved portion configured to prevent said second curved portion from passing through the external orifice of the cervix, inserting said elongated member connected to an intrauterine device into the cervix positioning said elongated member so that the second curved portion rests at the entrance of the cervix, stabilizing said elongated member by adjusting the second curved portion and adjusting the first curved portion so that the elongated member rests comfortably. In this embodiment, the method further comprises the step of removing said intrauterine device by pulling the elongated member at the first curved portion. In another embodiment, the intrauterine device is removed by pulling the elongated member at the second curved portion.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

What is claimed is:

1. An intrauterine device string for attachment to an intrauterine device for a female, the female having a cervix comprising an endocervical canal and an external orifice, the intrauterine device string comprising:
   an elongated member with an upper portion, an intermediate portion, and a lower portion;
   wherein said upper portion is configured to attach said elongated member to the intrauterine device,
   wherein said intermediate portion is configured to extend through the endocervical canal, and
   wherein said lower portion comprises a first curved portion configured to follow a contour of the external orifice of the cervix; and
   a second curved portion at an end of said lower portion having a memory-retaining material to prevent said second curved portion from passing through the external orifice of the cervix and to constrain said second curved portion to follow the contour of the outer portion of the cervix; and
   wherein said intermediate portion is configured to pass through a plane defined by three points on said second curved portion when in use.

2. The intrauterine device string of claim 1, wherein said elongated member is a single continuous piece.

3. The intrauterine device string of claim 1, wherein said second curved portion is a loop.

4. The intrauterine device string of claim 3, wherein said loop is a closed loop.

5. The intrauterine device string of claim 4, wherein said elongated member is flexible.

6. The intrauterine device string of claim 1, further comprising means for adjusting the shape of said first curved portion.

7. The intrauterine device string of claim 1, wherein said first curved portion is flexible.

8. The intrauterine device string of claim 1, wherein said first curved portion is movable to one of a plurality of different positions on said lower portion.

9. The intrauterine device string of claim 1, wherein said elongated member comprises a metal coating.

10. The intrauterine device string of claim 1, further comprising means for adjusting a shape of said second curved portion.

11. The intrauterine device string of claim 1, wherein said elongated member further comprises a memory-retaining material.

12. The intrauterine device string of claim 1, wherein said second curved portion comprises a spiral.

13. The intrauterine device string of claim 12, wherein said first curved portion further comprises a relatively malleable metallic inner core.

14. The intrauterine device string of claim 1, wherein second curved portion is thicker in diameter than said upper portion.

15. The intrauterine device string of claim 1, wherein said second curved portion comprises a proximal end and a distal end and wherein the second curved portion increases in thickness from said proximal end to said distal end.

16. A method, comprising:
providing an intrauterine device attached to an intrauterine device string, the intrauterine device string comprising an elongated member with an upper portion, an intermediate portion, and a lower portion;
wherein said upper portion is configured to attach said elongated member to the intrauterine device, wherein said intermediate portion is configured to extend through the endocervical canal, and
wherein said lower portion comprises a first curved portion configured to follow a contour of the external orifice of the cervix; and
a second curved portion at an end of said lower portion having a memory-retaining material to prevent said second curved portion from passing through the external orifice of the cervix and to constrain said second curved portion to follow the contour of the outer portion of the cervix; and
wherein said intermediate portion is configured to pass through a plane defined by three points on said second curved portion when in use.
inserting said elongated member into the cervix such that the intrauterine device rests in the uterus;
positioning said elongated member in the cervix such that said second curved portion rests outside of the external orifice of the cervix; and
adjusting said second curved portion wherein said elongated member is stabilized in the cervix.

* * * * *